United States Patent [19]

Su

[11] Patent Number: 4,528,111

[45] Date of Patent: Jul. 9, 1985

[54] SHAVING CREAM GEL CONTAINING INTERPOLYMER REACTION PRODUCT OF SELECTED CATIONIC POLYMERS AND ANIONIC POLYMERS

[75] Inventor: Dean T. Su, North Brunswick, N.J.

[73] Assignee: Colgate-Palmolive Company, New York, N.Y.

[21] Appl. No.: 564,591

[22] Filed: Dec. 22, 1983

[51] Int. Cl.$^3$ .................. C11D 1/02; C11D 1/38; A61K 7/06; A61K 31/74

[52] U.S. Cl. .................................... 252/107; 252/90; 252/118; 252/173; 252/174.17; 252/DIG. 5; 252/DIG. 14; 252/543; 424/70; 424/73; 424/78; 424/81

[58] Field of Search ................. 252/118, 90, DIG. 14, 252/173, 543, DIG. 5, 174.17, 107; 424/70, 73, 78, 81

[56] References Cited

U.S. PATENT DOCUMENTS

| | | | |
|---|---|---|---|
| 1,940,026 | 12/1933 | Smith | 424/73 |
| 3,541,581 | 11/1967 | Monson | 424/73 |
| 3,959,566 | 5/1976 | Pangonis | 428/446 |
| 3,988,438 | 10/1976 | Weinstein | 424/70 X |
| 4,145,411 | 3/1979 | Mende | 424/45 |
| 4,219,535 | 8/1980 | Sugahara et al. | 252/135 X |
| 4,238,346 | 12/1980 | Sugahara et al. | 252/140 X |
| 4,239,631 | 12/1980 | Brown | 252/DIG. 14 |
| 4,240,450 | 12/1980 | Grollier et al. | 424/70 |
| 4,405,489 | 9/1983 | Sisbarro | 252/DIG. 13 X |
| 4,412,026 | 10/1983 | Collins | 524/354 |
| 4,412,027 | 10/1983 | Klein et al. | 524/364 |

FOREIGN PATENT DOCUMENTS

| | | | |
|---|---|---|---|
| 0034126 | 8/1981 | European Pat. Off. | 434/73 |
| 2098226 | 11/1982 | United Kingdom . | |

OTHER PUBLICATIONS

"Cosmetics Science and Technology", second edition, vols. 1, 2 and 3, ed. Balsam & Sagarin, John Wiley & Sons, 1974.

Primary Examiner—John E. Kittle
Assistant Examiner—Mukund J. Shah
Attorney, Agent, or Firm—Richard N. Miller; Murray M. Grill; Herbert S. Sylvester

[57] ABSTRACT

A stable shaving cream gel having superior foaming and after-feel characteristics containing as the essential ingredient a water soluble gel which is the interpolymer reaction product of a quaternized cationic polymer selected from the group consisting of poly(diallyldimethylammonium chloride-co-acrylamide) and a quaternary ammonium cellulose ether polymer, with an anionic polymer selected from the group consisting of a polysulfonic acid and alginic acid.

13 Claims, No Drawings

SHAVING CREAM GEL CONTAINING INTERPOLYMER REACTION PRODUCT OF SELECTED CATIONIC POLYMERS AND ANIONIC POLYMERS

This invention relates to a novel gel shaving cream composition comprising a higher fatty acid soap, a humectant, a hydrocarbon propellant, and as the essential ingredient a water soluble gel formed by the interpolymer reaction of selective anionic polymers with selective cationic polymers, in an aqueous medium.

DESCRIPTION OF THE PRIOR ART

The use of anionic polymers in cosmetic compositions is well known in the art as shown in U.S. Pat. No. 3,654,167 wherein is disclosed a hydrophilic gel reaction product of a polymeric fatty acid polyamide and a diethanolamide of a fatty acid useful as a detergent in bar form or as a clear gel shampoo. Said polymer reaction gel is water soluble (column 4 lines 35–39). The polyamide polymer reactant may be pretreated with other polymeric materials prior to the addition of the diethanolamide, such as acrylamide-acrylic acid copolymer, etc. (column 5 lines 33–50) resulting in a gel having novel and unique properties. This is a reaction of two anionic polymers. There is no mention herein of its use in a shaving cream. U.S. Pat. No. 4,128,631 discloses a clear anionic polymer gel of an acrylamido-sulfonic acid salt, useful as a lubricant in skin care compositions including preshave lotions and after shave products, (Examples VIII and IX). However, there is no disclosure of a shaving foam.

Likewise, the use of cationic polymers as conditioning agents for skin and hair treating compositions such as shampoos is well known in the prior art. U.S. Pat. No. 3,996,146 discloses a composition comprising a cationic quaternary polymer derived from dimethyl-diallylammonium salts (Merquat 100), at least two anionic detergents, at least one amphoteric detergent and acid to maintain a pH of about 4 to 6.7. U.S. Pat. No. 4,273,760 discloses shampoo compositions containing a cationic polymer, and anionic surfactants. U.S. Pat. No. 4,048,301 discloses a shampoo containing a water soluble graft cationic polymer and a detergent. U.S. Pat. No. 3,953,591 discloses a skin conditioning emulsion containing a quaternized cellulose ether polymer, a fatty acid or mixture of higher alkyl fatty acids and a polysiloxane fluid.

The use of both anionic and cationic polymers in skin treating compositions is also shown in the prior art in U.K. Patent Application No. 2,098,226A, wherein said polymers react on the hair, and may be added in a single composition or in two separate compositions.

The use in hair care compositions, of a water insoluble polyelectrolyte complex, formed by the reaction of a cationic polymer with an anionic polymer, in the form of a stable dispersion is disclosed in U.S. Pat. No. 4,299,817.

The reaction product of a cationic polymer and an anionic polymer in skin and hair treating compositions including shaving foams is disclosed in U.S. Pat. No. 4,240,450, wherein said reaction product may be preformed or be formed on the hair.

U.S. Pat. No. 3,541,581 discloses a cleansing composition useful in shaving foams, shampoos, hand cleansers and pharmaceutical preparations, in the form of a stable post-forming gel containing water, water soluble soap, volatile liquid post-foaming agent and a water soluble gelling agent derived from naturally occurring substances such as cellulose, sucrose and glucose.

None of the aforecited prior art discloses a shaving composition of superior foaming and after-feel characteristics containing as the essential ingredient, the water soluble gel reaction product formed by the interaction of a selective anionic polymer and a selective cationic polymer, more specifically defined in copending patent application Ser. No. 564,589 by Dean T. Su filed of even date.

The Journal of Polymer Science, Vol. 14 (1976) 767–771, which is hereby incorporated by reference, discloses gel formation through interpolymer interaction of poly(methacrylic acid) and poly(vinylbenzyl-trimethylammonium chloride) under specific solution concentrations. Otherwise, precipitation occurs. It is further noted herein, that the gel structure of the interpolymer complex formed at 30° C. in an aqueous medium is irreversibly altered at elevated temperatures as evidenced by its decreased viscosity. However, no irreversible change during heating is observed in an alcoholic medium; and the concentrations to effect gelation instead of precipitation therein is different from that in an aqueous medium. This article clearly illustrates the specific conditions required to form an interpolymer gel by the interaction of specific anionic and cationic polymers.

SUMMARY OF THE INVENTION

It has now been found that the addition to a shaving cream comprising a higher fatty acid soap, a humectant, and a hydrocarbon propellant in an aqueous medium, of a water soluble interpolymer gel free of precipitates prepared through the interpolymer reaction of selective anionic polymers with selective cationic polymers under specific conditions of speed and concentration in an aqueous medium free of interfering ingredients, results in a shaving gel with superior foam characteristics, slip and after-feel properties.

Accordingly, it is a primary object of the present invention to prepare a shaving cream gel with a new gel system provided by the interpolymer gel reaction products of selective anionic polymers, and selective cationic polymers.

Another object of this invention is to provide a shaving cream gel with superior smooth foaming characteristics.

Still another object of this invention is to provide a shaving cream gel with good skin substantivity.

Another object of this invention is to provide a stable shaving cream gel having good slip and after-feel characteristics.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

To achieve the foregoing and other objects and in accordance with the present invention, as embodied and broadly described herein, the novel shaving cream gel of this invention comprises a major amount of water, a higher fatty acid soap, a humectant, a hydrocarbon propellant and a preformed water soluble interpolymer gel reaction product formed by the rapid and intensive interaction of two oppositely charged selective polymers; a quaternized cationic polymer bearing positive charges and selected from the group consisting of poly(diallyldimethylchloride-co-acrylamide) and a quaternary ammonium cellulose ether polymer, and an anionic polymer bearing negative charges and selected from the group consisting of poly(2-acrylamido-2-methylpropane sulfonic acid) and alginic acid.

More specifically, the shaving cream gel of this invention comprises, by weight, a fatty acid soap, preferably made in situ by the reaction of about 3–20%, preferably 5–14%, of at least one fatty acid having at least 8 carbon atoms, with about 0.1–15% of a base selected from the group consisting of monoethanolamine, diethanolamine, triethanolamine, sodium hydroxide and potassium hydroxide; about 1–20%, preferably 1.5–10%, of at least one humectant selected from the group consisting of propylene glycol, glycerine and sorbitol; about 0.5–10% of at least one hydrocarbon propellant selected from the group consisting of propane, n-pentane, isopentane, neopentane, n-butane, isobutane and mixtures thereof; about 0.05–5%, preferably 0.1–1.0%, of a water soluble interpolymer gel reaction product of a quaternized cationic polymer selected from the group consisting of poly(diallyldimethyl chloride-co-acrylamide) and a quaternary ammonium cellulose ether polymer, and an anionic polymer selected from the group consisting of poly(2-acrylamido-2-methylpropane sulfonic acid) and alginic acid; and about 55–94% water.

The method of preparing the interpolymer gels used in present novel shaving cream gel comprises the rapid mixing, at a rate of at least 1000 rpm, of high concentrations of aforesaid selective anionic and selective cationic polymers in an aqueous medium substantially free of interfering ingredients such as salt, amphoteric, anionic and cationic compounds.

More specifically, aqueous solutions of the cationic polymer are admixed with an aqueous solution of the anionic polymer, or either the anionic polymer or the cationic polymer in powdered form may be added to an aqueous solution of the oppositely charged polymer and vigorously mixed. The order of addition is immaterial, provided the essential conditions of speed and concentration are present and the specific group of polymers are used as reactants in the production of the polyelectrolyte complex in the form of a clear gel, free of precipitates. A hazy gel is indicative of the presence of precipitates. The interpolymer gels prepared in accordance herewith are stable, i.e. they retain their gel structure under conditions of heating or cooling and return to their original viscosity at room temperature. After the gel is formed, it can be thinned without losing its gel structure. The interpolymer gel may be thick and viscous and non-pourable or substantially non-pourable, or be of a lesser viscosity and pourable.

The selective group of quaternized cationic polymers used in the preparation of the water soluble interpolymer gels are water soluble and include:

1. Poly(diallyldimethylammonium chloride-co-acrylamide), which is the copolymer of dimethyldiallylammonium chloride and of acrylamide, having a molecular weight of more than 500,000, and sold under the name Merquat 550 and Merquat S by the Merck Company and obtainable as an 8% aqueous solution. This polymer has the following main chain constituent:

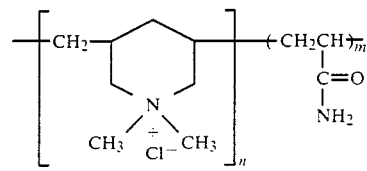

These cyclopolymers are described in U.S. Pat. Nos. 3,912,808, 3,986,825 and 4,027,008 incorporated by reference. The homopolymers and copolymers of aforesaid formulae can be prepared as described in U.S. Pat. Nos. 2,926,161, 3,288,770 or 3,412,013, the disclosure of these various patents being hereby included by reference.

2. Quaternary derivatives of cellulose ethers, described in U.S. Pat. No. 3,472,840, having a molecular weight of 100,000 to 3,000,000, available from Union Carbide under the tradename, Polymer JR in powdered form, having the structural formula:

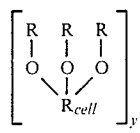

wherein $R_{cell}$ is the radical of an anhydroglucose unit, y is a number having a value of, say, 50 to 20,000 and each R individually represents a substituent which is a group of the general formula:

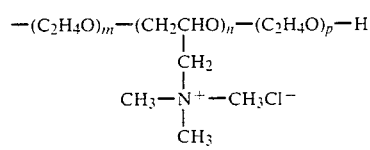

wherein m is an integer from 0 to 10, n is an integer from 1 to 3, and p is an integer from 0 to 10. The viscosity of the "JR" Polymer ethers may vary from 50 to 35,000 centipoises at 25° C. in 2% by weight aqueous solutions when measured by ASTM method D-2364-65 (Model LVF Brookfield, 30 rpm, Spindle 2).

The selective group of anionic polymers include:

1. Polysulfonic acid (PSA) such as poly(2-acrylamido-2-methylpropane sulfonic acid) available as Polymer HSP 1180 from Henkel as a 15% aqueous solution, having the following structure:

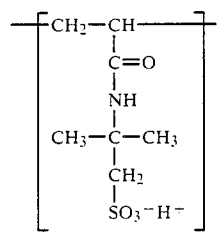

2. Alginic acid in free acid form, which is water insoluble and available as a powder, having the following structural formula:

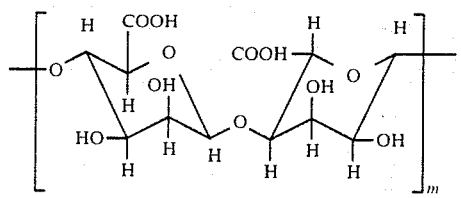

The interpolymer reactions of polycationic and polyanionic materials produce reaction products ranging from insoluble precipitates to water soluble and water insoluble but swellable gels. The reaction product of poly(2-acrylamido-2-methylpropane sulfonic acid) (PSA) and Merquat 550 loses its fluidity and forms a clear gel at 7.5% PSA and 4% Merquat 550, while the individual solutions flow freely. The minimum concentration required for the formation of the interpolymer gel reaction product of PSA and Merquat 550 is 7.5% PSA and 4% Merquat 550. The aqueous reaction mixture, which is the sum total of both solutions, contains 3.75% PSA and 2% Merquat 550. The gel, when diluted to 1.89% PSA and 0.96% Merquat 550, still exhibits a high viscosity of more than 24,000 cps, while the individual solutions show a viscosity of 400 cps and 200 cps, respectively. This gel is prepared by mixing vigorously a 7.5-15% solution of PSA and 4-8% solution of Merquat 550. Slow mixing results in white precipitates within the gel. Further dilution of the two solutions before mixing also results in white precipitates when they are mixed. This clearly indicates that it requires fast and intensive interactions of the two opposite charges to insure maximum amount of ion pair formation to give the gel structure. Whether the gel is water soluble or water insoluble depends on the formation of intimate or loose ion pairs which, in turn, depends on the charge density and structure of the polyelectrolytes.

The fast and intensive interactions of the two oppositely charged polymers necessary in the production of a gel as opposed to a precipitate, require the essential reaction conditions of vigorous mixing of at least 1000 rpm, and selective anionic and cationic polymers in aqueous solutions containing minimal concentrations of at least about 1% and preferably 1.25% by weight of cationic polymer, depending on the specific polymer reactants.

The intermolecular reactions of anionic polymers and cationic polymers resulting in the formation of gels of various types, ranging from water soluble to water insoluble depend on both the reaction conditions and the polymer structures. Viscosities of the reaction products of poly(2-acrylamido-2-methylpropane sulfonic acid) (I) and poly(diallyldimethylammonium chloride-co-acrylamide) (II) increased from 3,100 cps at 1.8% (I) and 0.24% (II) to 24,850 cps at 1.89% (I) and 0.96% (II). At 7.5% (I) and 4% (II) the reaction product loses its fluidity entirely and forms a clear, water soluble gel. Polymer (I) and cationic cellulose ether polymer (IV) also form a clear, water soluble gel at 5% (I) and 3.33% (IV). A minimum concentration of 3.8% (I) and 1.25% (IV) is required to form a gel, which results in a final concentration of 1.9% (about 2%) polymer (I) and 0.6% polymer (IV) in the reaction mixture. Polymer (II) forms a water soluble gel with the water insoluble, free acid form of alginic acid (V) at 1% (V) and 4% (II).

The resulting interpolymer gels are elastic and continuous in nature and capable of absorbing water in the formation of a very thick viscosity. Likewise, they retain their gel structure even upon dilution. They are stable and retain their gel structure when subjected to heat and/or cold. In addition, the viscosity of the gel does not permanently change as a result of heating and/or cooling. This unexpected feature is not possessed by the interpolymer gel disclosed in the cited *The Journal of Polymer Science*, (1976), wherein the viscosity thereof decreased permanently upon heating, and the final viscosity is determined by the temperature at which heating is stopped (page 770).

The presence of the water soluble interpolymer gel reaction product formed by the rapid and intensive interaction of oppositely charged selective polymers provides the novel shaving cream gel of this invention with unique and unexpected properties of skin substantivity, improved slip and after-feel properties, as well as being used for overall foam improvement and making the gel shaving cream stringy. This formula is based on a high concentration of soap and other materials such as sorbitol, and every ingredient contributes to the final viscosity of the shaving cream. Only a very small amount of gel (less than 0.19% PSA and 0.1% Merquat 550) is used in the formula. It does slightly increase the final viscosity but mostly it makes the shaving cream more stringy rather than thicker. It significantly improves the foam characteristics and makes the after-feel smoother. The water soluble interpolymer gel is a critical component of present novel shaving cream gel.

The amount of water soluble interpolymer gel in the shaving cream gel of this invention constitutes about 0.05–5% and preferably 0.1–1.0% by weight. Amounts in excess of 5% results in a hazy gel which is too thick, and too substantive to the skin. Amounts less than 0.05% affords insufficient thickening of the shaving cream, and inadequate skin substantivity resulting in poor after-feel properties.

The major essential component of this shaving gel is about 55–94%, preferably 65–85%, by weight of water which may be deionized or distilled water free of dissolved electrolytes such as salts and acids. The water component is essential in the preparation of present stable shaving gel having desirable foaming properties and capable of being readily rinsed from the skin. Water possesses adequate solubility for the interpolymer gel reaction product, and adequate compatibility with the other essential ingredients, namely the fatty acid soap, and the humectant.

An essential ingredient of present shaving cream gel is at least one carboxylic acid soap having at least 8 carbon atoms, which may be preformed, or formed in situ by reacting about 3–20% and preferably 5–14% of at least one carboxylic acid having the formula:

$$R_1(OC_nH_{2n})_m R_2\text{—COOH}$$

wherein $R_1$ is an alkyl radical of $C_6$–$C_{16}$, $n=2$–3, $m=0$–20, and $R_2=OCH_2$ to $OC_3H_6$ or $CH_2$ to $C_3H_6$, with about 0.1–15% of at least one base or alkali selected from the group consisting of monoethanolamine, diethanolamine, triethanolamine, sodium hydroxide and potassium hydroxide. Suitable fatty acids include stearic, coconut oil fatty acids, palmitic, myristic, oleic, lauric, ricinoleic. The fatty acid soap constitutes about 4–30%, preferably 8–18%, by weight of the shaving gel. Amounts of soap in excess of 30% produces an undesirable furry foam, and soap in an amount less than 4% yields a shaving gel of insufficient foam volume.

Another essential ingredient of present shaving cream gel constitutes at least one humectant selected from the group consisting of propylene glycol, glycerine and sorbitol in amounts of at least about 1% to a maximum of about 20% and preferably 1.5–10% by weight of the total composition. Amounts in excess of 20% yield a shaving product which has too thick a viscosity, a greasy after-feel on the skin and cannot easily be washed from the skin. Amounts less than 0.5% produce a shaving product that delivers an undesirable drier shaving foam.

Another essential ingredient of present shaving cream gel constitutes about 0.5–10% and preferably 1.5–4% by weight of at least one hydrocarbon selected from the group consisting of n-pentane, isopentane, neopentane, n-butane and isobutane. Mixtures of n-pentane and n-butane, or isopentane and neopentane, or isopentane and isobutane are particularly desirable. Amounts in excess of 10% produces too much foaming and the shaving cream gel product is delivered as a foam and not as a gel. Amounts less than 0.5% produces a product which does not foam fast enough after delivery on the skin, significantly delaying the production of foam.

Optionally preferred ingredients include about 0.1–5% by weight of one or more fatty acid esters having the general formula:

$$R_1(OCR_2)_n$$
(with C=O)

wherein $R_1$ is a radical selected from the group consisting of $C_1$–$C_4$ alkyl or alkylene, $C_1$–$C_4$ hydroxyalkyl or hydroxyalkylene, polyhydroxyalkyl or polyhydroxyalkylene of 6 to 30 carbon atoms, polyethylene glycol and polypropylene glycol; $R_2$ is a $C_8$–$C_{18}$ alkyl radical and $n=1$ or 2. The presence of esters such as ethylene glycol distearate produce an opaque gel. The presence of the esters in the shaving gel effects a denser foam and a smooth feel on the skin. Suitable esters include polyethylene glycol distearate, glyceryl monostearate, polyglyceryl-3 diisostearate, etc.

Another optionally preferred ingredient which improves skin feel is an organic alcohol of the general formula:

$$R_1(C_2H_4O)_nOH$$

wherein $R_1$ is a saturated or unsaturated $C_8$–$C_{18}$ radical and n is 0–30. Amounts of about 0.1–5% by weight of one or more fatty alcohols may be added, such as ethoxylated (21 ethoxides) stearyl alcohol, ethoxylated (5 ethoxyides) oleic alcohol, cetyl alcohol.

Various compatible additives which do not adversely affect the gel structure of present shaving gel may be added in minor amounts such as perfume, coloring materials, opacifiers, antiseptic agents, water-soluble thickening or gelling agents, e.g., polyethylenoxide, hydroxyethyl cellulose, etc., preservatives and the like. The presence of electrolytes including inorganic chloride salts such as potassium chloride, sodium chloride and ammonium chloride should be avoided because they may adversely affect the gel.

The pH of these semi-transparent shaving gels is at least 7 and may be within the range of about 7 to 10, preferably 8 to 9.

The shaving gels of present invention are generally prepared by melting the solid fatty acid(s) together with the solid fatty ester and solid fatty alcohol, if used, by heating above their melting point to about 140°–170° F.; adding to said hot liquified fatty acid a heated solution of humectant and water and mixing about 3 minutes to form an oil dispersion; adding a heated aqueous solution of a base to the hot oil dispersion with mixing to form the soap.

A semi-transparent micro-emulsion is formed at said elevated temperature of 170° F., which becomes an opaque macro-emulsion at low temperatures. The base may be added to the fatty acid prior to the humectant addition, and the humectant per se (minus water) may be added to the soap mixture or to the fatty acid. The preformed interpolymer gel is added to the hot emulsion and agitated preferably for about 10 minutes. The mixture cools down to about 140° F. Mixing is continued and the mixture is cooled to about 90°–95° F., yielding a thin macro-emulsion. At this point the fragrance and/or color, if used, is added and the mixture is cooled to room temperature and refrigerated at 40° F. overnight. At this low temperature the mixture becomes thick and non-flowable. The hydrocarbon, in liquid form, is added with rapid agitation to the thick mixture at or below 40° F., resulting in the formation of a semi-transparent (colloid) gel. If more than one hydrocarbon is added to the thick, non-flowable mixture at or below 40° F., they are added sequentially without destroying the semi-transparent final gel product. Some of the liquid hydrocarbon may vaporize with a concomitant loss in hydrocarbon gas. The resultant gel is placed in a sealed container and may be dispensed from a pressurized aerosol container or extruded from collapsible metal tubes, or the like.

DETAILED DESCRIPTION OF THE INVENTION

The following examples are merely illustrative of the invention, and are not to be construed as limiting thereof.

EXAMPLE 1

| Gel Shaving Cream | |
|---|---|
| Ingredients | Weight (g) |
| Part A | |
| Stearic acid | 100 |
| Polyglyceryl-3 diisostearate | 30 |
| Cetyl alcohol | 30 |
| Part B | |
| Triethanolamine | 80 |
| D.I. Water | 660 |
| Part C | |
| Glycerine | 100 |
| Part D | |
| Interpolymer gel[1] | |
| PSA (15% A.I.) | 12.6 |
| Polymer JR-400 (5% A.I.) | 15 |
| D.I. Water | 72.4 |
| Part E | |
| Pentane | 10 |

[1] Interpolymer gel formed by rapid and intensive interaction of Poly (2-acrylamido-2-methylpropane sulfonic acid) with a quaternary ammonium cellulose ether polymer in an aqueous medium, having a viscosity of 30,550 cps at 77° F. (Brookfield RVF #3 2 rpm).

Part A solid ingredients are heated to 160° F. to form a liquid. Part B ingredients are heated to 150° F. and the hot solution is slowly added to Part A while stirring to form a soap. This mixture is cooled to 120° F. Glycerine (Part C) is added and mixed for 5 minutes resulting in the formation of a micro-emulsion.

110 g of the resultant emulsion is mixed with 40 g of the preformed interpolymer gel (Part D) and stirred until homogeneous. The viscosity is fairly high. The addition with mixing of 10 g of pentane (Part E), forms a good semi-transparent gel which has good slip, and foaming properties.

EXAMPLE 2

| Ingredients | Weight (g) |
| --- | --- |
| Part A | |
| Stearic acid | 100 |
| Polyglyceryl-3-diisostearate | 30 |
| Oleth-5[1] | 5 |
| Glycerine | 100 |
| Part B | |
| Triethanolamine (99%) | 80 |
| D.I. Water | 685 |
| Part C | |
| Interpolymer gel[2] | |
| 1:3 PSA (15% A.I.): JR-400 (5% A.I.) | 10 |
| D.I. Water | 10 |
| Part D | |
| Pentane | 10 |

[1]Oleyl alcohol ethoxylated with 5 ethoxides
[2]The water is mixed with the gel until the gel is completely swollen Part A solid ingredients are heated to 160° F. to form a liquid, and slowly added to Part B ingredients heated to 150° F., while stirring. The resultant mixture is a micro-emulsion.

100 g of this micro-emulsion is mixed with preformed Part C and Part D (pentane), yielding a semi-transparent shaving gel which exhibits thick, creamy foam having good slip and no roll-up.

EXAMPLE 3

| Ingredients | Weight (g) |
| --- | --- |
| Part A | |
| Palmitic acid | 110 |
| PEG-150 distearate | 20 |
| Brij 99[1] | 10 |
| Sorbitol | 30 |
| Part B | |
| Triethanolamine | 70 |
| D.I. Water | 855 |
| Part C | |
| PSA polymer (15% solu.) | 1.5 |
| Merquat S polymer[2] (8% solu.) | 1.5 |
| D.I. Water | 40 |
| Part D | |
| Butane/Pentane (25/75) | 7 |

[1]Oleyl alcohol ethoxylated with 20 ethoxides
[2]poly(diallyldimethylammonium chloride-co-acrylamide)

Part A ingredients are heated to 150° F. to melt the solid ingredients and form a liquid and then cooled to 140° F.

Part B is separately heated to 140° F.

Part A is added with stirring to heated Part B. The resultant soap formula is a micro-emulsion.

Part C polymers are vigorously mixed before adding the water. A specific interpolymer is formed, which is added with stirring to 150 g of the micro-emulsion, followed by the addition with mixing of Part D.

The resulting semi-transparent shaving cream gel provides good foam which is slightly dry.

EXAMPLE 4

| Ingredients | Weight (g) |
| --- | --- |
| Part A | |
| Palmitic acid | 100 |
| Part B | |
| PEG-45M (Polyox WSR N-60K)[1] | 1 |
| Propylene glycol | 8 |
| Part C | |
| Sorbitol solution[a] | 25 |
| Triethanolamine (99%) | 75 |
| D.I. Water | 791 |
| Part D | |
| PSA Polymer (15%) | 1.5 |
| Merquat 550 (8%) | 1.5 |
| D.I. Water | 40 |
| Part E | |
| Butane/Pentane (25/75) | 5 |

[1]polyethylene oxide, H(OCH$_2$CH$_2$)$_n$OH, where n has an average value of 45,000

Part A is heated to 140° F.

Part C ingredients are heated to 130° F. and added to Part A to form the palmitic acid soap.

Part B ingredients are thoroughly mixed and added to and mixed with the soap mixture at room temperature. The resultant soap formula is in the form of a good thick emulsion.

Part D polymer ingredients are vigorously mixed before adding the water. The preformed viscous interpolymer gel is added to 150 g of the thick soap formula and mixed until homogeneous. Part E is added to and mixed with the viscous mixture yielding a semi-transparent gel which provides good slip and good foam.

EXAMPLE 5

| Soap Formula | wt. % | g |
| --- | --- | --- |
| Part A | | |
| Palmitic acid | 11.00 | 110.00 |
| PEG-150 distearate | 1.80 | 18.00 |
| Part B | | |
| Sorbitol solution[a] | 3.60 | 36.00 |
| Propylene glycol | 1.20 | 12.00 |
| PEG-45M | 0.18 | 1.80 |
| D.I. Water | 30.00 | 300.00 |
| Part C | | |
| Lemon oil | 0.10 | 1.00 |
| Part D | | |
| TEA (99%) | 6.00 | 60.00 |
| D.I. Water | 46.12 | 461.20 |

Heat Part A to 190° F., Part B to 170° F. and Part D to 170° F. Add Part B to Part A while stirring. Mix 10 minutes. Add Part D to Part A+Part B. Mix 10 minutes. Cool to 110° F. Add Part C to Part A+Part B+Part D.

A preformed interpolymer gel, formed by vigorously reacting 2.5 g PSA (15% solution) with 2.5 g Merquat S (8% solution), which is swelled by the addition of 60 g water, is added to and mixed with 150 g of the soap formula until homogeneous. 10 g of a mixture of a 3:1 pentane/butane is admixed, resulting in a semi-transparent shaving gel which provides an airy, smooth foam.

EXAMPLE 6

| Soap Formula | g |
| --- | --- |
| Part A | |

| Soap Formula | g |
| --- | --- |
| Palmitic acid | 110.00 |
| PEG-150 distearate | 16.00 |
| Part B | |
| Sorbitol solution[a] | 34.00 |
| Propylene glycol | 10.00 |
| PEG-45M (polyox WSR N-60K) | 1.50 |
| D.I. Water | 300.00 |
| Part C | |
| TEA (99%) | 60.00 |
| D.I. Water | 461.35 |
| Part D | |
| Fragrance K-44-621 | 6.00 |
| D & C Yellow #10 (1%) | 0.75 |
| F D & C Blue #1 (1%) | 0.40 |
| Part E | |
| Polymer PSA | 17.00 |
| Merquat S | 17.00 |
| D.I. Water | 470.00 |

Part A, Part B and Part C are separately heated to 180° F., 170° F. and 170° F. respectively. Add Part B to Part A and stir for 5 minutes. Add Part C to Part A+Part B and stir for 5 minutes. Add Part E at 115° F. and add Part D at 110° F. with minimum mixing.

To 200 g of the soap formula is added with mixing 10 g of a 3:1 mixture of pentane and butane. A semi-transparent shaving gel is formed which provides an airy, smooth foam of good viscosity.

EXAMPLE 7

| Soap Formula | g |
| --- | --- |
| Part A | |
| Palmitic acid | 105.00 |
| Sandopan DTC acid[1] | 10.00 |
| PEG-150 distearate | 10.00 |
| Sandoxylate SX 208[2] | 5.00 |
| Part B | |
| Sorbitol solution[a] | 18.00 |
| Propylene glycol | 10.00 |
| PEG-90M[3] | 1.00 |
| D.I. Water | 300.00 |
| Part C | |
| TEA (99%) | 60.00 |
| D.I. Water | 474.35 |
| Part D | |
| Fragrance | 5.00 |
| D & C Yellow #10 (1%) | 1.20 |
| F D & C Blue #1 (1%) | 0.45 |
| Part E | |
| Polymer PSA | 10.00 |
| Merquat S | 10.00 |
| D.I. Water | 530.00 |

[1]Trideceth-7 carboxylic acid, $CH_3(CH_2)_{11}CH_2O(C_2H_4O)_7CH_2COOH$
[2]Iso-$C_{10}H_{21}OC_3H_6O(C_2H_4O)_{\overline{11}}H$
[3]Polyethylene oxide. $H(OCH_2CH_2)_nOH$, where n has an average value of 90,000

Parts A, B, and C are separately heated to 180° F., 170° F. and 170° F. respectively. The fragrance is added at 110° F. and the dyes at 160° F. Preformed gel E is added at 160° F.

To 200 g of the soap composition is admixed 4 g pentane and 4 g butane. The resultant semi-transparent shaving gel provides a good, smooth, airy, non-dry foam of good viscosity.

EXAMPLE 8

| Soap Formula | g |
| --- | --- |
| Palmitic acid | 70.00 |
| PEG-75 distearate | 4.00 |
| Acetulan[1] | 4.00 |
| Sorbitol solution[a] | 20.00 |
| Glycerine | 20.00 |
| D.I. Water | 100.00 |
| TEA | 36.00 |
| D.I. Water | 271.10 |
| Fragrance | 3.00 |
| D & C Yellow #10 (1%) | 0.05 |
| F D & C Blue #1 (1%) | 0.25 |
| Polymer PSA | 12.00 |
| Merquat S | 12.00 |
| D.I. Water | 247.00 |

[1]Acetylated lanolin alcohol 8 g of neopentane is admixed with 200 g of the soap formula. The resulting shaving gel provides a good foam which is slightly thin.

EXAMPLE 9

| Soap Formula | Weight (g) | |
| --- | --- | --- |
| Palmitic acid | 82.00 | |
| Stearath-21[1] | 5.00 | |
| PEG-150 distearate | 1.80 | |
| Sorbitol solution[a] | 24.00 | |
| D.I. Water | 200.00 | |
| TEA (99%)[2] | 48.00 | |
| D.I. Water | 469.90 | |
| Fragrance | 3.20 | |
| D & C Yellow #10 (1%) | 0.80 | |
| F D & C Blue #1 (1%) | 0.30 | |
| Polymer PSA | 7.50 | preformed |
| Merquat S | 7.50 | interpolymer |
| D.I. Water | 150.00 | gel |

[1]Water insoluble ethoxylated (21 ethoxides) stearyl alcohol
[2]Triethanolamine To 200 g of the soap formula is added 1.5 g neopentane and 1.5 g butane with stirring. A semi-transparent gel of good viscosity is formed which delivers a good non-dry, smooth foam in good volume.

EXAMPLE 10

| Soap Formula | Weight (g) | |
| --- | --- | --- |
| Part A | | |
| Palmitic acid | 82 | |
| Stearath-21 | 5 | |
| PEG-150 distearate | 1.9 | |
| Part B | | |
| Sorbitol solution | 24 | |
| D.I. Water | 200 | |
| Part C | | |
| TEA (99%) | 48 | |
| D.I. Water | 436 | |
| Part D | | |
| Fragrance | 3.2 | |
| D & C Yellow #10 (1%) | 0.8 | |
| F D & C Blue #1 (1%) | 0.3 | |
| Polymer PSA | 9 | performed |
| Merquat S | 9 | interpolymer |
| D.I. Water | 180 | gel |

Parts A, B and C are separately heated to 170° F. and mixed. Part D is premixed and then added. The fragrance and color are individually added lastly to the soap formula.

To 200 g of the soap formula is added with mixing 2–2.2 g neopentane and 2.6–2.9 n-butane. The resultant shaving gel is semi-transparent of good viscosity and delivers a smooth, continuous, non-dry foam having good volume.

All of the above shaving gels deliver a mixture of a viscous gel and smooth foam on the face, which is readily removable from the skin by rinsing with water, leaving a soft, smooth, and clean after-feel.

It is understood that the foregoing detailed description is given merely by way of illustration and that variations may be made therein without departing from the spirit of the invention. The "Abstract" given above is merely for the convenience of technical searchers and is not to be given any weight with respect to the scope of the invention.

It should be understood that the described shaving cream gels exhibit mechanical properties typical of the solid state, but have a yield value such that they resist flow up to a given shearing stress and flow above said stress. These gels are substantially homogeneous colloidal dispersions of at least the five essential components—soap, humectant, hydrocarbon, interpolymer and water. However, these gels are characterized by the property of being post foaming. For purposes of this invention, a post foaming gel can be defined as a gel which remains substantially free from foaming for at least about thirty seconds, more usually about sixty seconds, after such gel is discharged from a pressure tight container at about 75° F. and approximately one atmosphere of pressure. Foam appears to be created by the vaporization of the hydrocarbon component from the surface of the gel. The rate of foaming and the characteristics of the resultant foam—quantity, foam density and lubricity—are controlled by the nature and proportions of the essential ingredients, particularly the hydrocarbon component. Typically, the post foaming characteristics will be designed to correspond to the preferences of the majority of the users.

What is claimed is:

1. A stable shaving cream gel comprising 55% to 94% by weight of water; 4% to 30% by weight of a water soluble salt of a carboxylic acid having the formula:

$$R_1(OC_nH_{2n})_mR_2COOH$$

wherein $R_1$ is an alkyl radical of $C_6$–$C_{16}$, $n=2$ to 4, $m=0$–20 and $R_2=OCH_2$ to $OC_3H_6$ or $CH_2$ to $C_3H_6$; 1% to 20% by weight of at least one humectant selected from the group consisting of propylene glycol, glycerine and sorbitol; 0.5% to 10% by weight of at least one hydrocarbon propellant selected from the group consisting of n-pentane, isopentane, neopentane, n-butane and isobutane; and 0.05% to 5% by weight of a preformed, water soluble, interpolymer gel reaction product formed by the rapid and intensive agitation of a cationic polymer bearing a positive charge selected from the group consisting of poly(diallyldimethylammonium chloride-co-acrylamide) and a quaternary ammonium cellulose ether polymer and an anionic polymer bearing a negative charge selected from the group consisting of poly(2-acrylamido-2-methylpropane sulfonic acid) and alginic acid, said interpolymer gel being effective to improve the foam characteristics, slip and after-feel properties of said composition.

2. The shaving gel according to claim 1, which additionally includes about 0.1–5% by weight of at least one fatty acid ester having the formula:

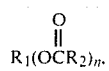

$$R_1(OCR_2)_n.$$

wherein $R_1$ is an alkyl radical or a polyhydric alkyl radical derived from glyceryl, polyglyceryl, sorbitol, polyethylene glycol or polypropylene glycol; $R_2$ is a $C_8$–$C_{18}$ alkyl radical, and $n=1$ or 2.

3. A shaving gel according to claim 1, which additionally contains about 0.1–5% by weight of a fatty alcohol having the formula:

$$R_1OH,$$

wherein $R_1$ is an alkyl radical or a polyhydric alkyl radical derived from glyceryl, polyglyceryl, sorbitol, polyethylene glycol or polypropylene glycol.

4. The shaving gel according to claim 1, wherein the water soluble interpolymer gel is the reaction product of at least 7.5% by weight of poly(2-acrylamido-2-methylpropane sulfonic acid) in water with at least 4% by weight of poly(diallyldimethylammonium chloride-co-acrylamide) in water.

5. The shaving gel of claim 1, wherein the water soluble interpolymer gel is the reaction product of at least 3.8% by weight of poly(2-acrylamido-2-methylpropane sulfonic acid) in water with at least 1.25% by weight of of a quaternary ammonium cellulose ether polymer in water.

6. The shaving gel according to clam 1, wherein the water soluble interpolymer gel is the reaction product of at least 1% by weight of alginic acid with at least 4% by weight of poly(diallyldimethylammonium chloride-co-acrylamide) in water.

7. The shaving gel according to claim 1, wherein the water soluble interpolymer gel is the reaction product of alginic acid with a quaternary ammonium cellulose ether polymer in an aqueous medium.

8. The shaving gel according to claim 1, wherein the hydrocarbon is a mixture of n-pentane of n-butane, isopentane and neopentane, or isopentane and isobutane.

9. The shaving gel according to claim 1, wherein the water soluble interpolymer gel constitutes about 0.1% to 1% by weight of the composition.

10. The shaving gel according to claim 1, which is free of the presence of electrolytes including inorganic salts and acids.

11. A shaving gel in accordance with claim 1 wherein said carboxylic acid salt is formed in situ by reacting about 3% to 20% by weight of said carboxylic acid with a base selected from the group consisting of monoethanolamine, diethanolamine, triethanolamine, sodium hydroxide and potassium hydroxide.

12. A shaving gel in accordance with claim 9 wherein said carboxylic acid salt is present in an amount of 8% to 18% by weight, said humectant is present in an amount of 1.5% to 10% by weight, said hydrocarbon is present in an amount of 1.5% to 4% by weight and water is present in an amount of 65% to 85% by weight.

13. A shaving gel in accordance with claim 12 wherein the water-soluble interpolymer gel is the reaction product of anionic poly(2 acrylamido-2-methylpropane sulfonic acid) polymer with cationic poly(diallyldimethylammonium chloride-co-acrylamide) polymer in an aqueous medium, the initial aqueous mixture containing at least 3.75% by weight of said anionic polymer and at least 2% by weight of said cationic polymer.

* * * * *